(12) United States Patent
von Oepen

(10) Patent No.: US 6,193,747 B1
(45) Date of Patent: Feb. 27, 2001

(54) STENT

(75) Inventor: Randolf von Oepen, Hirrlingen (DE)

(73) Assignee: Jomed Implantate GmbH, Rangendingen (DE)

( * ) Notice: Subject to any disclaimer, the term of this patent is extended or adjusted under 35 U.S.C. 154(b) by 0 days.

(21) Appl. No.: 09/171,293

(22) PCT Filed: Feb. 17, 1998

(86) PCT No.: PCT/EP98/00884

§ 371 Date: Oct. 16, 1998

§ 102(e) Date: Oct. 16, 1998

(87) PCT Pub. No.: WO98/35634

PCT Pub. Date: Aug. 20, 1998

(30) Foreign Application Priority Data

Feb. 17, 1997 (DE) .......................................... 297 02 671 U

(51) Int. Cl.[7] .......................................... A61F 2/00
(52) U.S. Cl. .......................................... 623/1.15
(58) Field of Search .................. 623/1, 11, 12, 623/1.1, 1.15, 1.17; 606/108, 191, 194, 195, 198

(56) References Cited

U.S. PATENT DOCUMENTS

| | | | |
|---|---|---|---|
| 5,776,183 | * | 7/1998 | Kanesaka et al. .................. 606/194 |
| 5,807,404 | * | 9/1998 | Richter ...................................... 623/1 |
| 5,810,872 | * | 9/1998 | Kanesaka et al. .................. 606/198 |
| 5,827,321 | * | 10/1998 | Roubin et al. ....................... 606/195 |
| 5,836,964 | * | 11/1998 | Richter et al. ....................... 606/194 |
| 5,855,600 | * | 1/1999 | Alt ......................................... 623/12 |
| 5,861,027 | * | 1/1999 | Trapp ................................... 606/198 |
| 5,868,781 | * | 2/1999 | Killion ................................. 606/198 |
| 5,876,449 | * | 3/1999 | Starck et al. .......................... 623/12 |
| 5,895,406 | * | 4/1999 | Gray et al. .......................... 606/198 |
| 5,922,021 | * | 7/1999 | Jang ....................................... 623/12 |

* cited by examiner

*Primary Examiner*—Michael J. Milano
(74) *Attorney, Agent, or Firm*—Shinjyu Global IP Counselors

(57) ABSTRACT

A stent (1) has a tubular flexible body (2) with the wall (3) having a web structure (4). The web structure (4) of the wall (3) has cells formed by a pair of adjacent sinuous web patterns (5,6) that are interconnected by linking elements (22) to form elastic elements.

11 Claims, 9 Drawing Sheets

STENT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to a stent.

2. Description of the Related Art

A stent is a medico-technical device which is inserted and guided to restricted portions of body vessels or body orifices and in its expanded state expands and keeps expanded the restricted portion at such a place. To this end, a stent must be extremely flexible in its non-expanded state so that upon introduction into the body vessels it can easily follow the windings of said vessels. Furthermore, the stent in its expanded state must be sufficiently stable to maintain the desired degree of expansion.

Although the generic stent (DE 296 08 037.1) already meets these requirements in a satisfactory manner, a further improvement of the stent characteristics is in principle desirable.

It is therefore the object of the present invention to provide a stent comprising a tubular, flexible body whose wall has a web structure, whose characteristics regarding flexibility in the non-expanded state and dimensional stability in the expanded state are further improved.

BRIEF SUMMARY OF THE INVENTION

The inventive stent is characterized by an improvement of its characteristics which as such are opposed, i.e., high flexibility in the non-expanded state and high dimensional stability in the expanded state.

The stent according to the invention provides a construction whose web structure comprises a plurality of adjoining cells. In different embodiments the web structure may be composed of webs or legs which have different structures and surround cells.

According to the invention at least one spring element is provided per cell. The spring element can for instance be a U- or V-shaped loop in one of the webs or legs of each cell. Hence, it is possible with the invention to form a multicellular stent which comprises a plurality of e.g. diamond-like cells or at least cells that resemble diamonds. The legs or webs which surround the cells or diamonds may here comprise the spring elements which in the non-spread state permit sufficient flexibility across the longitudinal axis.

BRIEF DESCRIPTION OF THE DRAWINGS

Further details, features and advantages of the invention will become apparent from the following description of embodiments taken in conjunction with the drawing, in which.

DETAILED DESCRIPTION OF THE INVENTION

Figure 1:
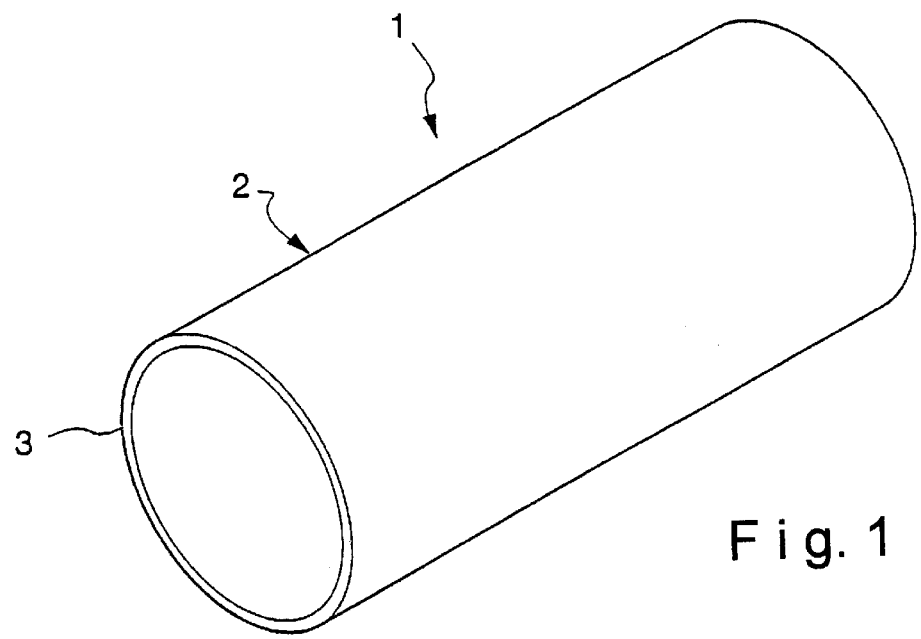
FIG. 1 is a schematically strongly simplified representation of the basic structure of a stent according to the invention.

FIG. 1 shows the basic structure of an inventive stent 1 which comprises a flexible, tubular body 2 having a wall 3, of which the front side is visible in FIG. 1.

Figure 2A:
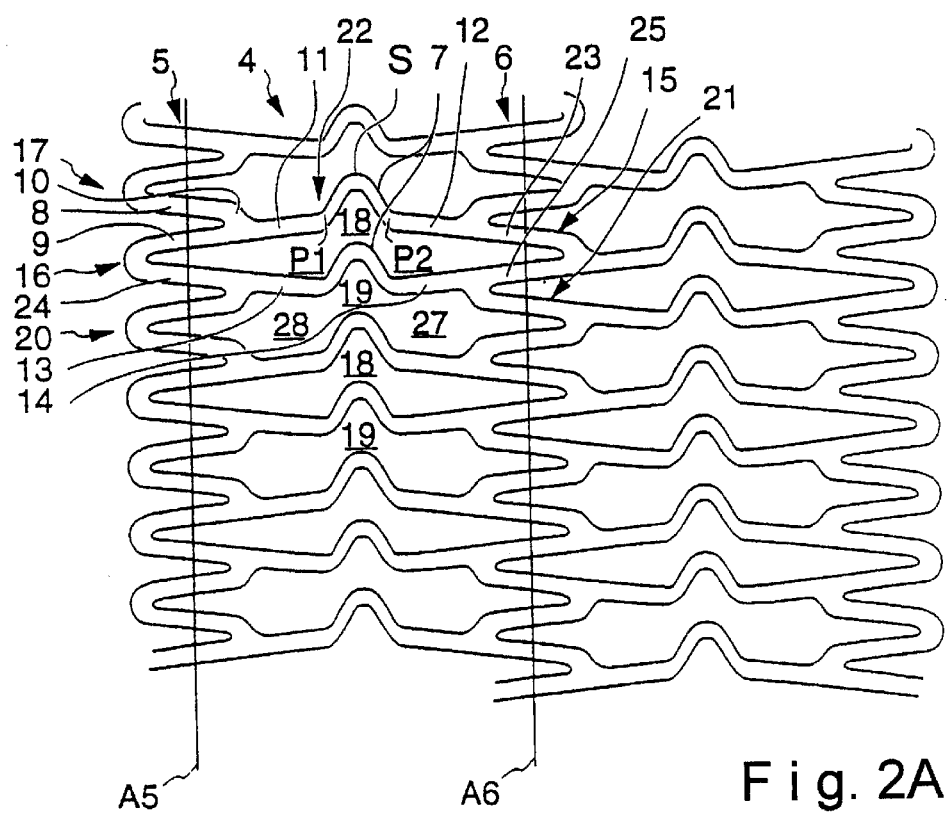
FIG. 2A is a view corresponding to FIG. 1, which shows the web structure of the wall of the stent according to FIG. 1.

FIG. 2A illustrates how a web structure 4 forming wall 3 is composed, the web structure 4, however, being not shown in detail in FIG. 1 for simplifying the drawing. Therefore, as far as the construction of the web structure 4 is concerned, reference is explicitly made in the following to FIG. 2A.

Depending on the size of the stent 1, the web structure 4 comprises a plurality of adjacently arranged and wound (also called meander-like) web patterns, of which FIG. 2A shows web patterns 5 and 6 with reference numerals by way of representation. As illustrated in FIG. 2A, the web patterns 5, 6 extend in a sinusoidally wound fashion and are oriented such that their axis $A_5$ and $A_6$ which are perpendicular to the cylindrical lateral surfaces of body 2 are arranged in parallel with one another.

The web patterns (of which only the web patterns 5, 6 are referred to in the following text by way of representation) have each a plurality of web loops, of which the web loops 15, 16 and 17 are provided with reference numerals in FIG. 2A. As follows from the wound course, these web loops alternately open to the left and to the right side according to the representation chosen in FIG. 2A.

The web patterns 5, 6 set up cells via respective spring elements, with a spring element being shown in FIG. 2A by way of representation and provided with reference numeral 22 in its entirety. The element 22 comprises two straight webs 11, 12 and a hairpin-shaped web arc 7. The web arc 7 has a vertex S and bases $P_1$, $P_2$. The straight webs 11, 12 follow bases $P_1$ and $P_2$, respectively, and extend to the respectively adjacent web patterns, i.e., in the state shown in FIG. 2A to web pattern 5 (web 11) and to web pattern 6 (web 12), respectively.

As is also illustrated in FIG. 2A, each of the web loops, in turn, comprises two straight webs 8, 9 and a bent web section 10 connecting said webs 8, 9. Webs 8 and 9 enclose an acute angle. As for webs 11 and 12, these members pass in straight fashion into web 9 of web loop 17 (web 11) and into web 23 of web loop 15 (web 12) of the web pattern 6. In the case of the element which is the next downwardly adjoining element, the left web 13 of said element passes into web 24 of web loop 16. The web 14 which is arranged at the other side of the next web arc 7 passes into web 25 of the web loop 15. A shown in FIG. 2, the webs 11 and 12 are slightly oriented downwards, whilst webs 13 and 14 are slightly oriented upwards.

The webs 11, 12, 13 and 14 and the two associated web arcs 7 enclose a cell or chamber 18. Chamber 19 which is positioned thereunder is again defined by webs and web arcs. Due to the fact that the two web loops 20 and 21 depart in the transition area between the webs of the elements and the webs of the associated web loops, one obtains a different form for a chamber 19 which at both sides of the web arc 7 comprises extended chamber regions 27 and 28. FIG. 2A illustrates that the chambers 18 and 19 follow one another in alternate fashion, with the chamber regions 27 and 28 being each enlarged in comparison with the chamber regions of the chamber 18 to the right and left side of the associated web arc 7.

FIG. 2A also illustrates that the vertices S of all web arcs 7 (in FIG. 2 only a web arc 7 with an associated vertex S is provided with reference numerals by way of representation) are all oriented into the same direction. It is also possible that all of the web arcs 7 have the same size or preferably have different alternating sizes or heights and widths.

Figure 2B:
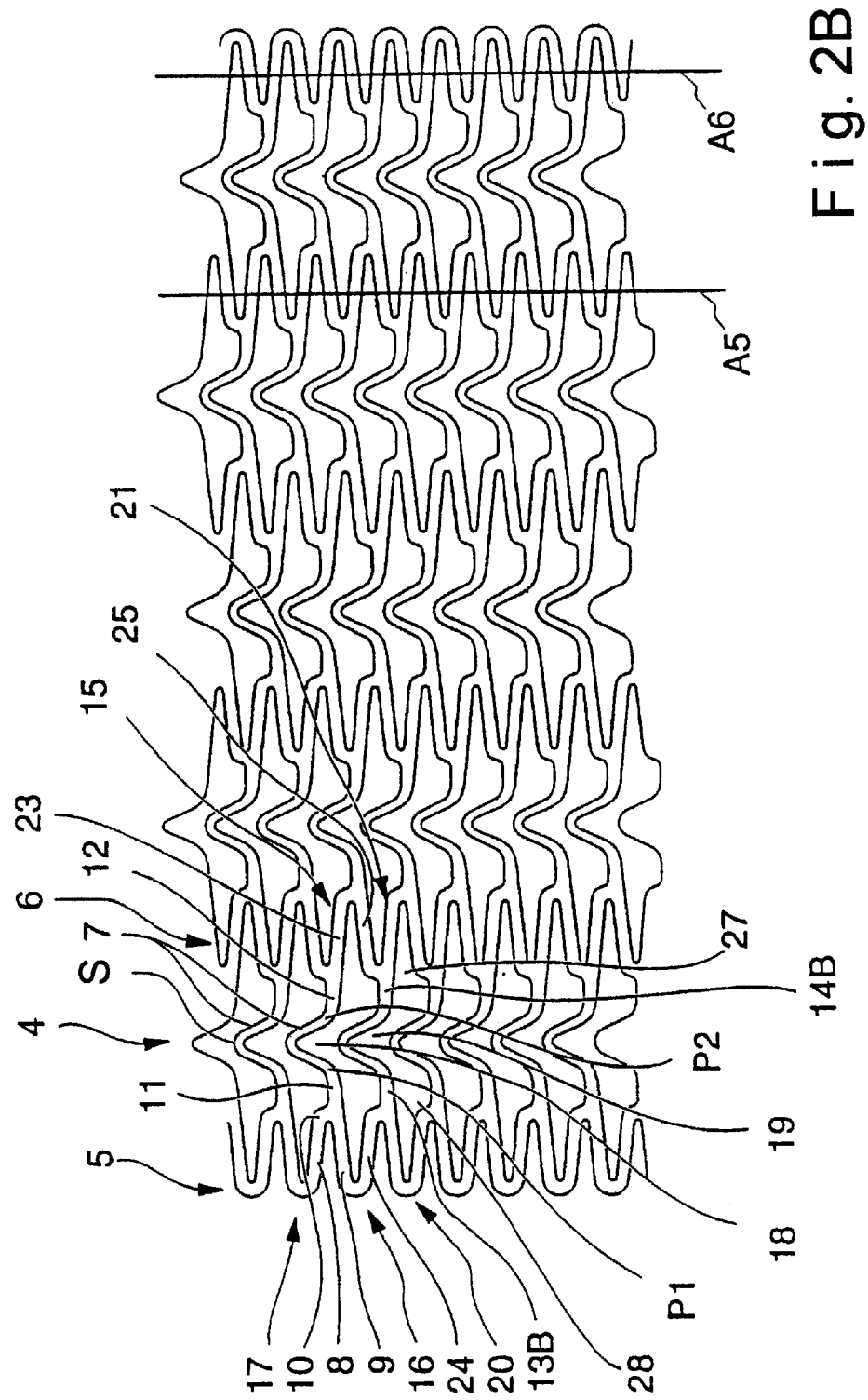
FIG. 2B is a view corresponding to FIG. 2A, which shows a modification of the web structure of the wall of the stent according to FIG. 2A.

FIG. 2B shows a modification of the embodiment according to FIG. 2A. In principle the embodiment shown in FIG. 2B is the same as that in FIG. 2A, so that all corresponding parts are provided with the same reference numerals as in FIG. 2A. In this respect reference can be made to the preceding description regarding FIG. 2A. The difference between the embodiments of FIG. 2A and FIG. 2B is that all webs extend upwardly towards the web arcs 7 according to the illustration chosen in FIG. 2B. To illustrate the difference between the embodiments according to FIG. 2A and FIG. 2B, the pair of webs 13 is provided in FIG. 2B with the index "B". In other words, this means that all of the webs towards the web arcs 7 are oriented in the same direction, for instance all face upwards, so that they are all in parallel with one another. By contrast, in the embodiment of FIG. 2A, the webs alternately extend upwards and downwards. The embodiment according to FIG. 2B has the advantage that the cells 18, 19 set up by the webs are each identical across their circumference and length. In addition to the written disclosure, reference is explicitly made to the drawing with respect to the disclosure of the web pattern and web structure of FIG. 2B.

Figure 3:
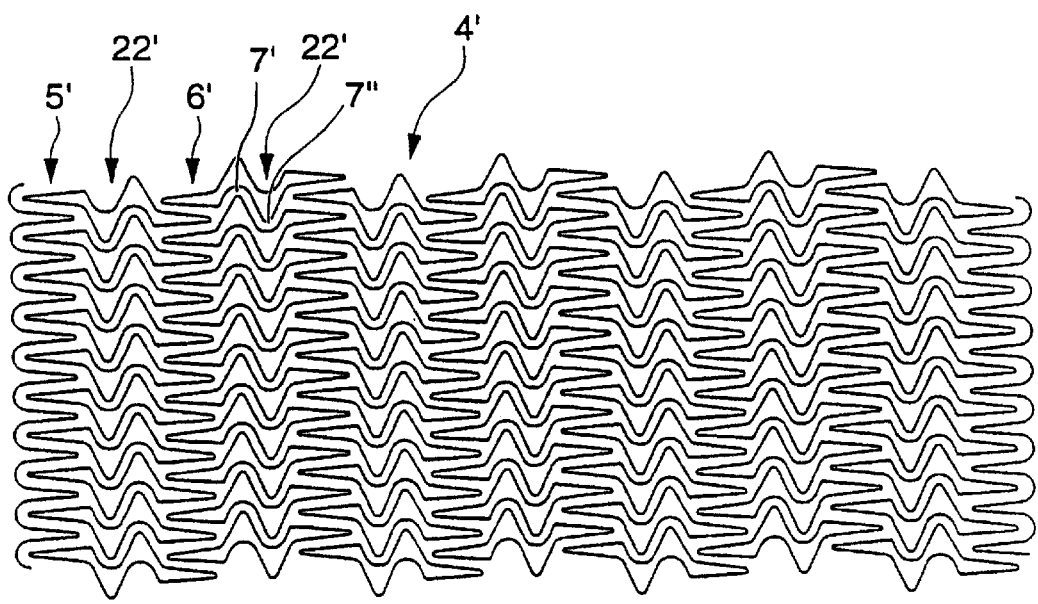
FIG. 3 is a view corresponding to FIG. 2, which shows an alternative embodiment of a web structure.

FIG. 3 shows an alternative embodiment of a web structure 4' which, in turn, comprises sinusoidally shaped web patterns 5' and 6' which extend next to one another in meander-like fashion and set up a cell with spring elements 22'. In this embodiment the elements 22' have S-shaped spring sections and thus web arcs 7' and 7" arranged one after the other, whose vertices are respectively oriented into different directions. As illustrated in FIG. 3, the vertices of elements 22' and their web arcs 7', 7", respectively, are alternately oriented (when viewed from the left to the right in FIG. 3). Apart from that, as regards all of the corresponding features, reference can be made to the embodiment of FIG. 2, especially as regards the structure of the web patterns 5', 6'. FIG. 3 shows the non-expanded state whereas FIG. 4 illustrates the expanded state of the web pattern 4' in which an alternately upwardly and downwardly oriented arrangement of the chambers is obtained between the web patterns and the elements, such a definition following from a sequence of the chambers when viewed from the left to the right in FIG. 4.

Figure 4:
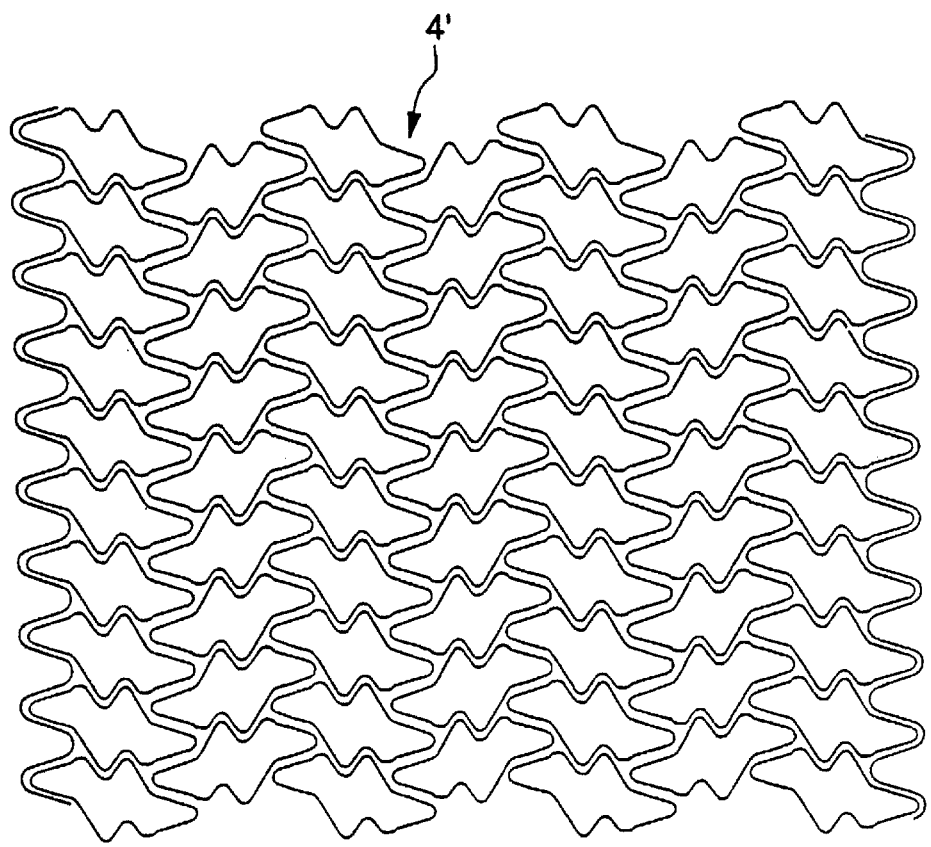
FIG. 4 shows the web structure according to FIG. 3 in the expanded state.

Both the embodiment according to FIG. 2 and according to FIGS. 3 and 4 can be obtained by cutting the respective web pattern by means of a laser assembly in a small metal tube.

Figure 5:
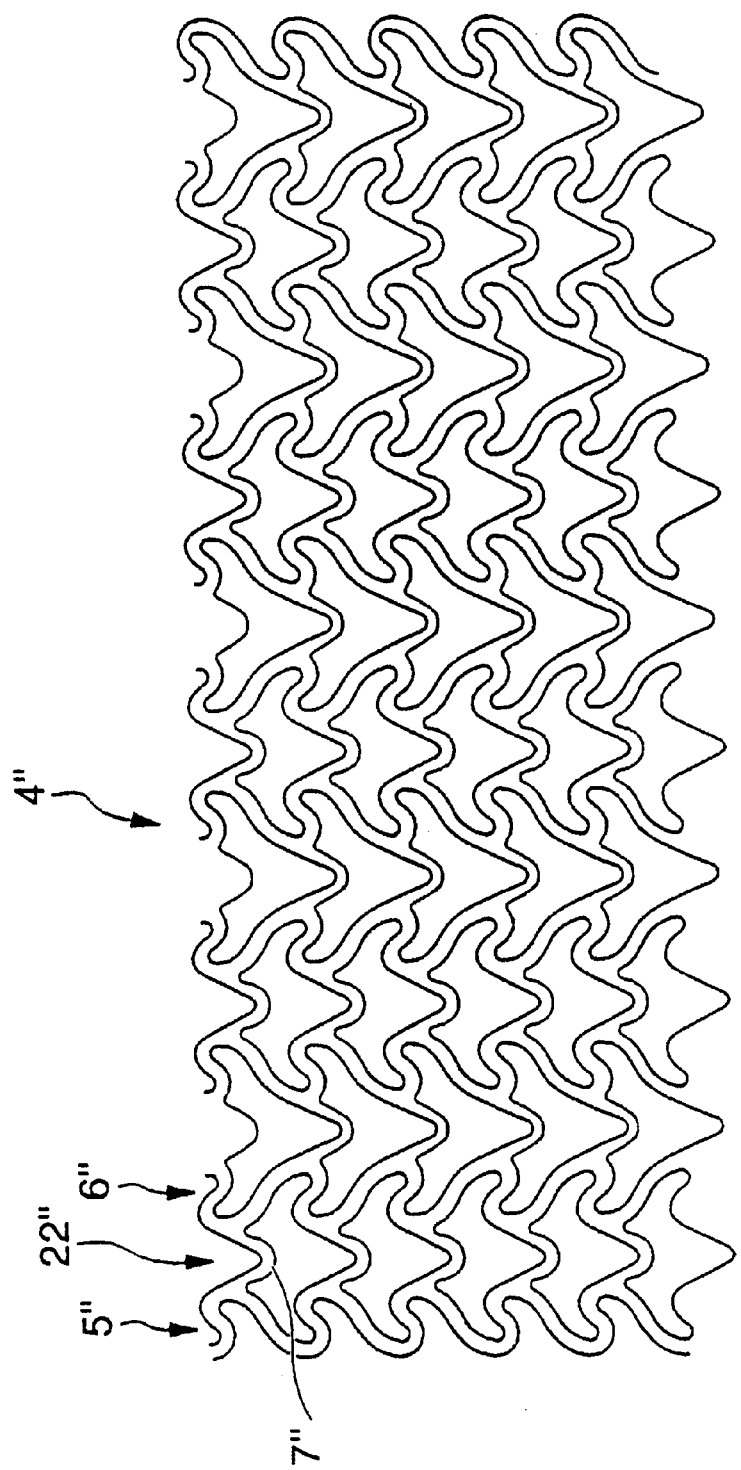
FIG. 5 shows a variant of the embodiment of FIG. 2.

FIG. 5 shows an embodiment of a web structure 4'' for the stent according to FIG. 1, with the embodiment essentially corresponding to the embodiment of FIG. 2. Therefore, the corresponding reference numerals which regard the web structure, the web patterns, the web arcs and the spring elements are provided with the same reference numerals as in FIG. 2, but with two primes. The web patterns 5'', 6'' are more wound or undercut than the web patterns 5, 6 of FIG. 2 to form a plurality of S-shaped segments having first and second loop sections, and the spring elements 22'' directly set up cells with the web patterns 5', 6''. In addition to the written disclosure, reference is explicitly made to the representation of FIG. 5 for reasons of disclosure.

Figure 6:
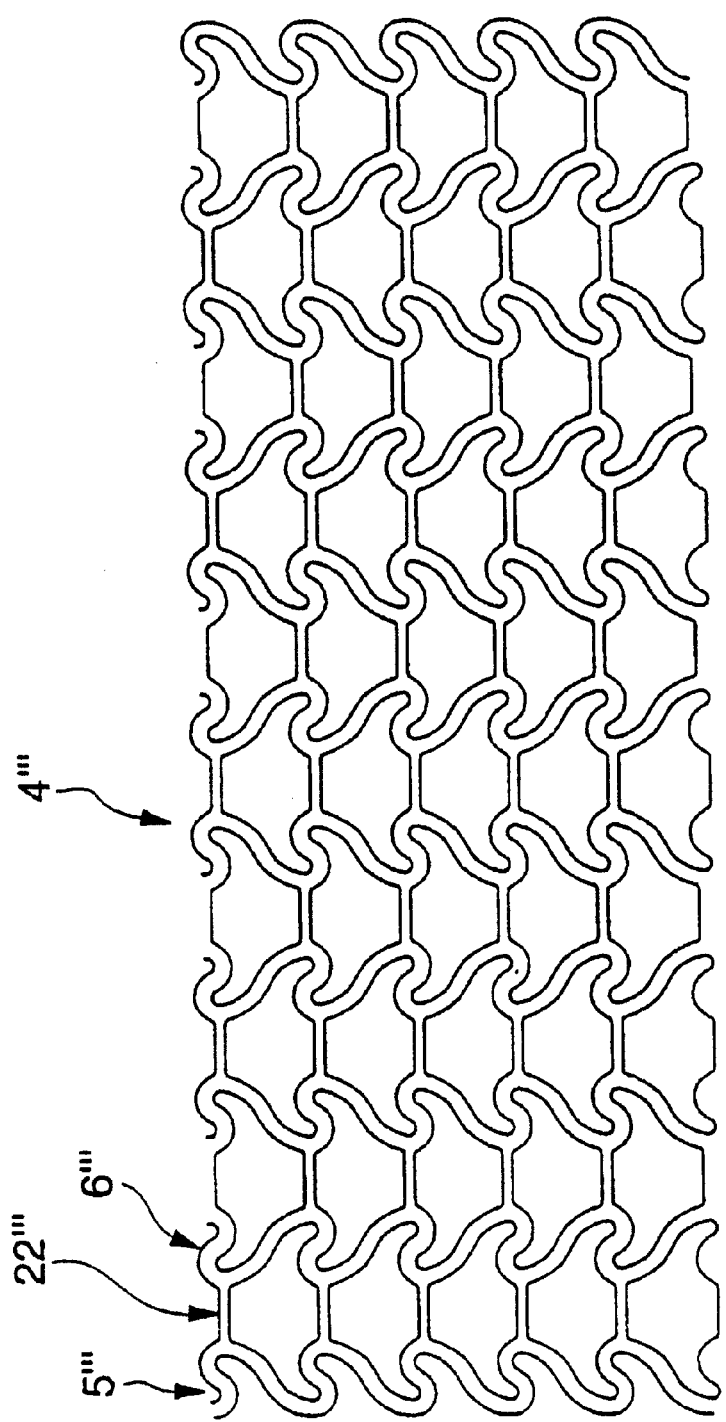
FIG. 6 shows a further variant of the embodiment of FIG. 2.

FIG. 6 is a variant web structure 4''' of the embodiment of FIG. 5. The web patterns 5''', 6''' are substantially identical with the embodiment according to FIG. 5. The spring elements 22''', however, are shaped as straight webs. In this embodiment, too, explicit reference is made to the illustration of FIG. 6 for the purpose of disclosure.

Figure 7:
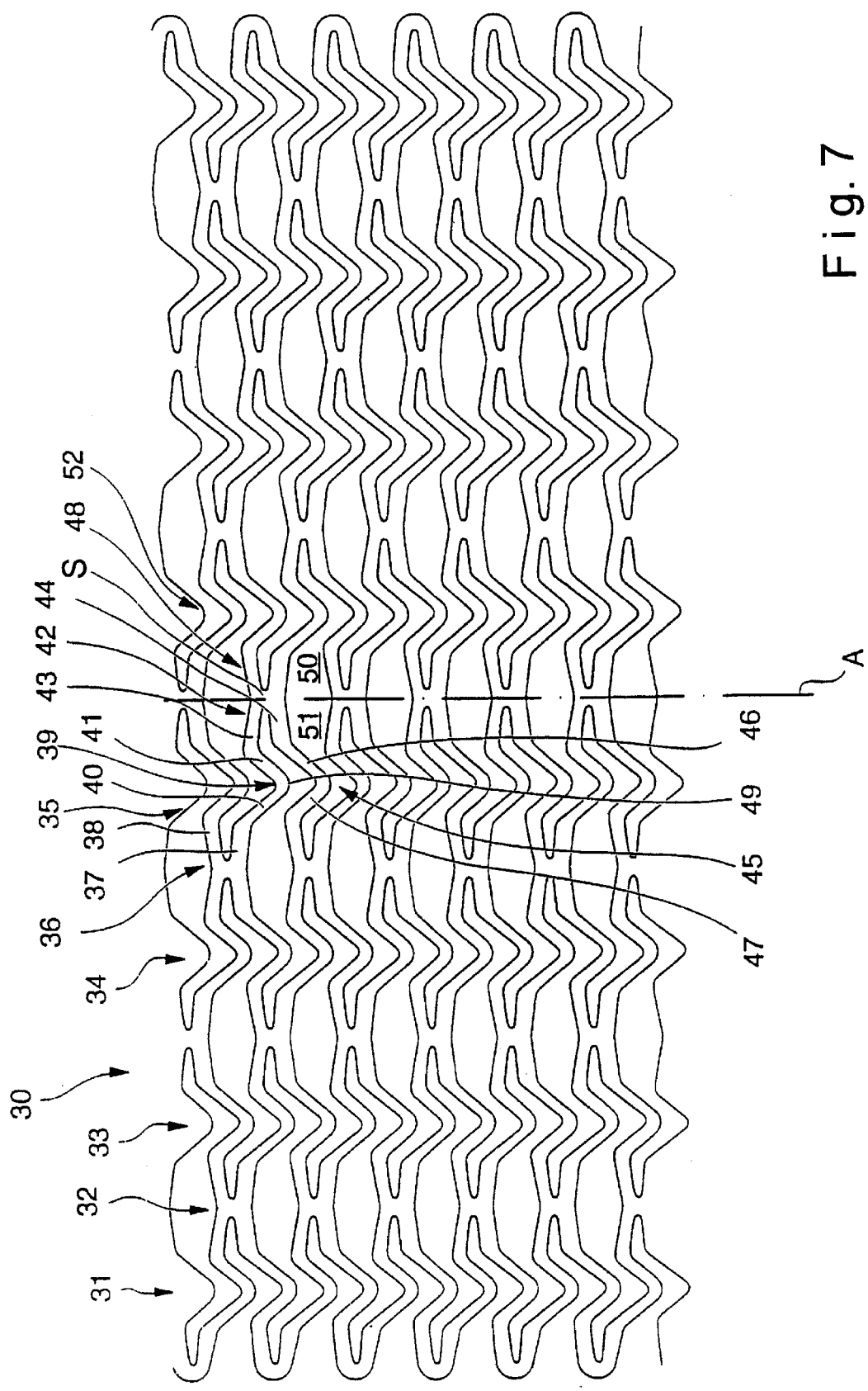
FIG. 7 is a view corresponding to FIG. 2, which shows a further embodiment of a web structure of the wall of the stent according to FIG. 1.

FIG. 7 shows a further embodiment of a web structure 30 for a stent according to FIG. 1. In this illustration of FIG. 7, a section of the wall of the tubular web is illustrated in a planar view. The stent with the web pattern according to FIG. 7 can be designated as a multicellular stent which is composed of diamonds. Each of these diamonds is provided in each leg with a U- or V-shaped spring element which in the non-expanded state guarantees a certain flexibility across the longitudinal axis.

To be more specific, the web structure 30 comprises a plurality of adjacently arranged web patterns, of which in FIG. 7 the web patterns 31, 33, 34, 35 and 52 are marked with corresponding reference numerals. These web patterns form radially extending wall structures on account of the tubular shape of the stent. As has been illustrated with reference to the example of the web patterns 31 and 33 in FIG. 7, these patterns set up a respective cell with a spring element 32. As illustrated in FIG. 7, the elements 32 form integral parts of respectively adjacent web patterns. The structure of all web patterns of the web structure 30 will be explained in an exemplary manner in the following by reference to the web pattern 35.

The web pattern 35 has a first loop 36 which comprises two interconnected legs 37, 38 which are arranged at an acute angle with respect to one another. The first loop 36 is followed by a second loop 39 having straight legs 40, 41 which are also arranged at an acute angle relative to one another. The loop 39, in turn, is followed by a third loop 42 which comprises straight legs 43 and 44 arranged at an acute angle relative to one another. The third loop 42 is followed by a fourth loop 45 having legs 46 and 57 that are straight again. The legs 46 and 47 of the fourth loop 45 are also arranged at an acute angle relative to one another. In the embodiment illustrated in FIG. 7, the legs of the respective loops 36, 39, 42 and 45 have each an approximately V-shaped configuration. As a rule, a U-shaped configuration would also be possible. As is also illustrated in FIG. 7, a complete web pattern is of course formed by a recurring sequence of four loops in the above-described manner. The number of the loops depends on the respective size of the stent so that, depending on the respective stent diameter, closed rings which together with the elements 32 set up a respective cell are obtained through the sequence of the plurality of four loops.

Furthermore, FIG. 7 illustrates by way of a plotted axis A that the web pattern 52 which at the right side follows the above-described web pattern 35 is obtained by mirror-inverting or folding the web pattern 35 by 180°. Hence, a sequence of web patterns which are each inverted at an axis A is obtained for the whole web structure 30, as has previously been described with reference to the web patterns 35 and 52.

The connection between the web patterns 35 and 52 is illustrated in FIG. 7 by the example of the loops 42 of the web pattern 35 and 48 of the web pattern 52. There is a connection at the respective vertex S of these loops 42 and 48, respectively, with the vertices S being located on axis A in the example. At both sides of axis A there are cells with partial chambers 50 and 51 that form a diamond-like total chamber which is defined by the legs of the associated loops. Hence, the loops 42 and 58 give another example of a spring element corresponding to the element 32 which has already been explained above. In this case the elements 32 due to their construction form or comprise the spring elements assigned to the respective cells.

As is finally illustrated in FIG. 7, all of the vertices of the second loops 39, which open upwards according to the illustration chosen in FIG. 7, are oriented in the same direction in the illustrated embodiment, with vertex 49 being plotted for the purpose of illustration. Hence, all of the vertices point downwards in the example because of the illustration chosen in FIG. 7.

Furthermore, all of the vertices of the first loops 36, which open to the right in FIG. 7, are oriented towards the left side while the vertices of the loops 42, which open to the left, are oriented towards the right side. The reverse case is respectively applicable to the mirror-inverted web patterns, as e.g. in web pattern 52. In addition to the written disclosure, explicit reference is here also made to the drawing of FIG. 7 with respect to the description and disclosure of web pattern 30.

Figure 8:
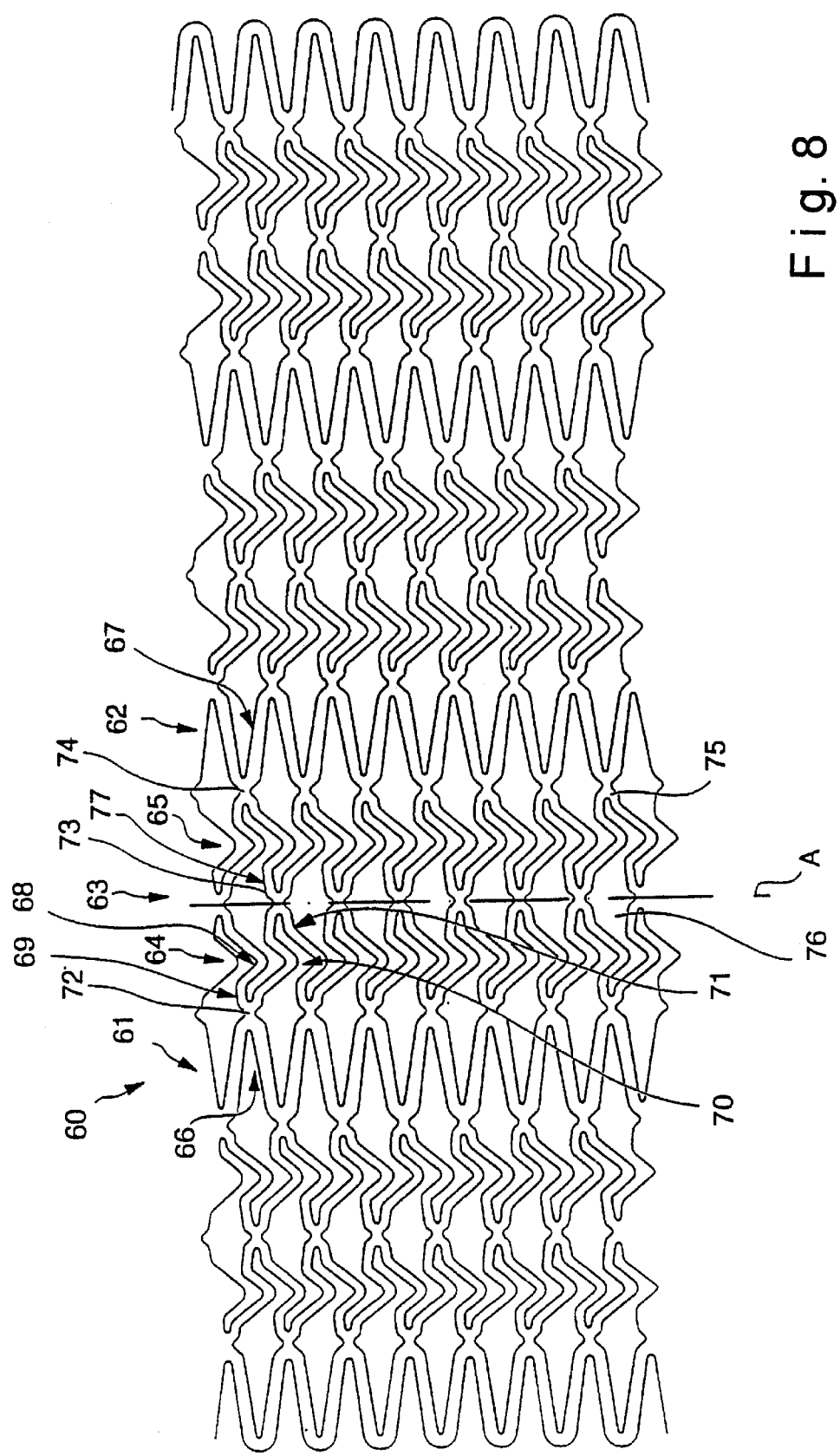
FIG. 8 is a view corresponding to FIG. 7, which shows a further embodiment.

FIG. 8 shows a further embodiment of a web structure 60 for the stent according to FIG. 1. This embodiment as shown in FIG. 8 is a planar representation of part of the stent wall. This further embodiment can be described as a stent which comprises individual, radially extending web patterns (extending in meander-fashion or in accordance with a sine curve) which are coupled with one another via diamonds which, in turn, are provided in each leg with a U- or alternatively V-shaped spring element which in the non-spread state guarantees the necessary flexibility across the longitudinal axis. Advantageously, the first web patterns (meanders) may be designed with a greater web width than the elements forming a cell with said patterns (to be still described), so that a high radial force can be received by the first web patterns. To be more specific, the web structure 60 according to FIG. 8 is composed as follows:

There are provided a plurality of sinusoidally shaped web patterns, of which the web patterns 61 and 62 are marked by way of example with reference numerals in FIG. 8. As illustrated in FIG. 8, the web patterns 61, 62 are arranged side by side and have substantially parallel axes. The web patterns 61 and 62 may be identical with a sine curve or at least have a similar course, so that they can also be designated as web patterns extending in meandering or wound fashion. Each is arranged out of phase by 180°, which with reference to the examples of the web patterns 61 and 62 means that a loop of the web pattern 61 which opens to the right is confronted with a loop of the web pattern 62 which opens to the left. It goes without saying that in this embodiment, too, the web patterns 61, 62 form rings of the stent wall in the actual tubular state of the stent, with a corresponding number of web patterns 61, 62 being of course provided in accordance with the length of the stent. In the following text, however, reference is always made by way of example to the web patterns 61, 62 for descriptive purposes.

Together with elements (spring elements) 63, these web patterns 61, 62 set up cells.

The element 63 is composed of two spring-element or web patterns 64, 65 in the illustrated embodiment. As illustrated in FIG. 8, the element web patterns 64, 65 are formed by mirror-inversion or folding on a symmetrical axis A. The element web patterns 64, 65 are each provided with four loops 68 to 71 that adjoin one another, whose structure with straight legs which are arranged at an acute angle relative to one another is comparable with the structure in FIG. 7, so that reference can be made in this respect to the preceding description. The loops 68 to 71 are each integrally connected with one another, so that the plurality of said loops yields the structure of the element web patterns. (As for the disclosure of said structure, explicit reference is again made to FIG. 8.)

FIG. 8 also shows that the web pattern 61 sets up a cell together with junctions respectively at the vertices of the loops thereof and with the element 63. A junction 72 is plotted by way of representation. The element web patterns 64 and 65 are interconnected through a plurality of junctions, which is symbolized by the junction 73. The subsequent web pattern 62 also sets up a cell with a plurality of junctions respectively at the vertex of its loops and with element 63, with a junction 74 being again plotted by way of representation. As illustrated in FIG. 8, the junction 72 is the vertex of a loop 66 of the web pattern 61 while the junction 74 is the vertex of a loop 67 of the web pattern 62.

As in the case of the embodiment of FIG. 7, the vertices of the loops 66 to 67 of the element web patterns are also oriented into the same direction. In this respect reference can be made to the comments regarding FIG. 7, with a vertex 75 of a loop of the right element web pattern 65 being plotted for easy understanding.

It should also be noted that the legs of the loops of the element web patterns 64, 65 each define cells 76 with associated spring elements. In this case, too, a chamber 76 is provided with this reference numeral in FIG. 8 for the purpose of representation.

Figure 9:
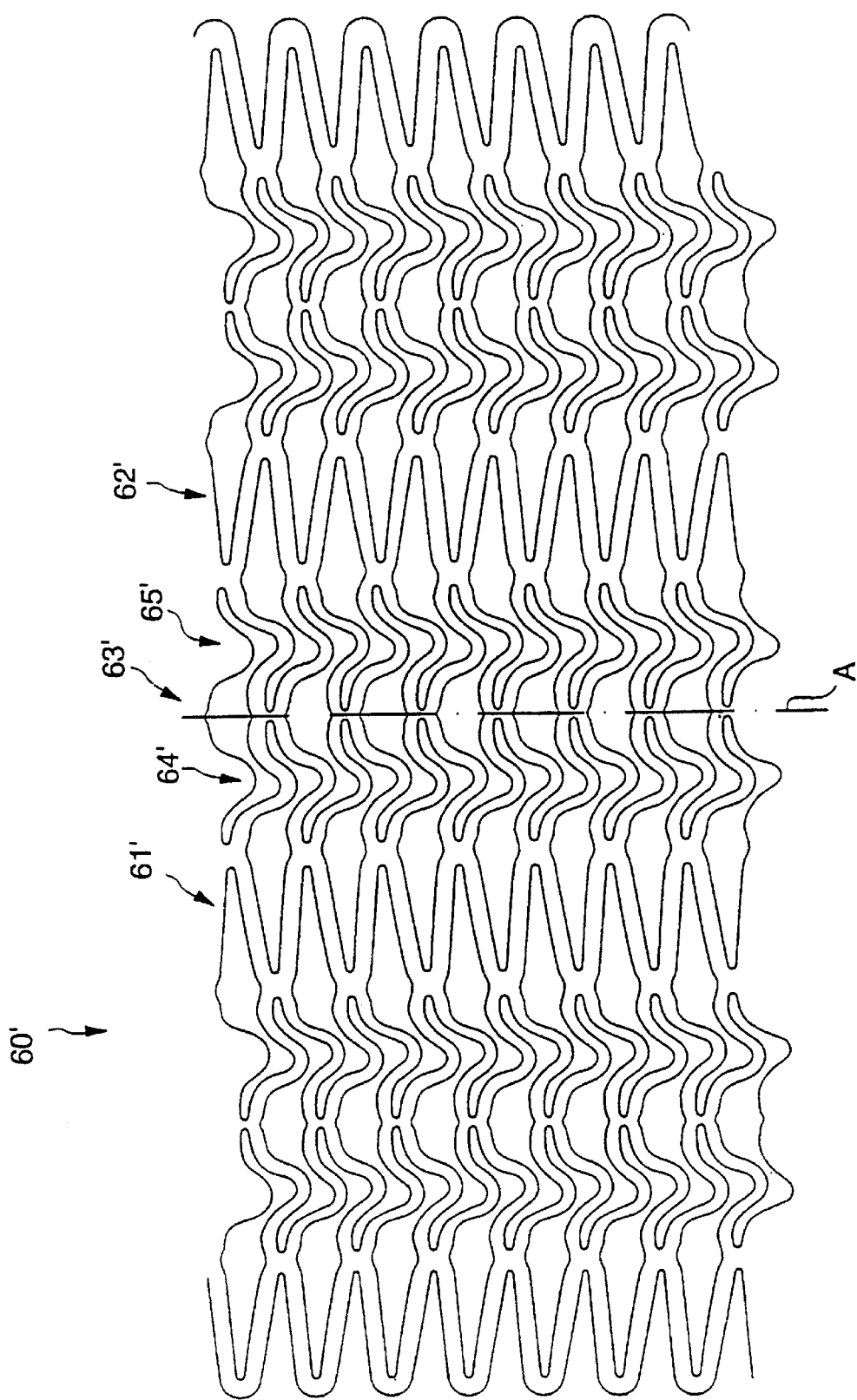
FIG. 9 is a view corresponding to FIG. 8, which shows a modification of the embodiment of the web structure according to FIG. 8.

FIG. 9 is substantially identical with the embodiment of FIG. 8, so that the reference numerals of the essential elements (single prime) are plotted according to the embodiment of FIG. 8. FIG. 9 illustrates that the element 63 or the loops thereof are slightly more rounded than in FIG. 8. Like in the case of the preceding embodiment, explicit reference is made to the drawing as to the disclosure of the web structure according to FIG. 9.

Figure 10:
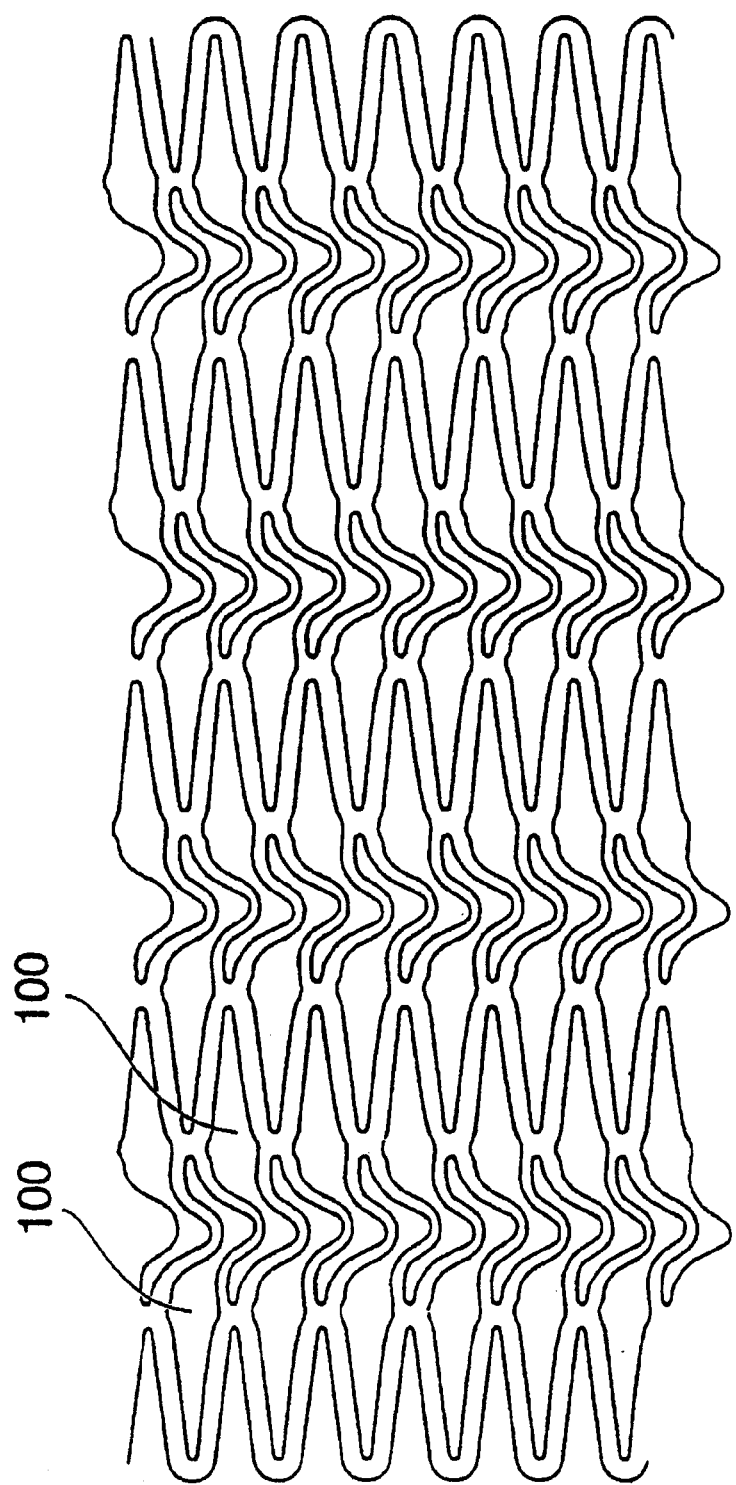
FIG. 10 shows a modification of the embodiment of FIG. 9.

Finally, FIG. 10 shows an embodiment of an inventive stent similar to FIG. 9. In this embodiment, exclusively uniform cells are set up, and only two cells are here provided with reference numeral 100 for the purpose of illustration.

In contrast to the embodiments 8 and 9, the webs enclose a cell such that a part of the cell consists of straight webs and a second part of webs which comprise each a spring element. The left part of a cell respectively forms the right part of the left and adjoining cell; the right part of a cell the respectively left part of the cell adjoining at the right side. The cells which are adjacent at the left and right sides are each turned by 180°, but are otherwise congruent.

Hence, FIG. 10 illustrates a stent which is composed of uniform cells, but in 2D representation the cells are respectively turned by 180°. A cell is always set up by two straight legs and two legs with spring elements. The spring elements in the legs ensure a high axial flexibility in the non-expanded state.

As for the various components, their design and function of said embodiment reference is made to the above explanations and embodiments.

What is claimed is:

1. An expandable stent comprising:

a tubular, flexible body whose wall has a web structure, said web structure including a plurality of adjoining cells which are surrounded by webs of said web structure with at least one spring element being provided per cell;

said spring elements being provided with web arcs which are shaped as hairpins and having a vertix and first and second bases, said first and second bases being followed by first and second webs that extends in straight fashion towards respectively neighboring web patterns, said web patterns being arranged with substantially parallel axes;

said web patterns being composed of a plurality of adjacently arranged web loops which have each two straight webs with a bent web section;

respectively adjacent spring elements defining cells that are differently shaped, with web loops passing into said elements; and one of said cells comprising extended cell portions next to the respective web arc.

2. An expandable stent comprising:

a tubular, flexible body formed by a wall with a web structure defining a plurality of adjoining cells that allows expansion of said body in a circumferential direction, said web structure including a plurality of sinusoidally shaped web patterns arranged in rings that are axially spaced apart, said sinusoidally shaped web patterns including a plurality of straight web sections with first web loops coupling adjacent first ends of said straight web sections together and second web loops coupling adjacent second ends of said straight web sections together, a plurality of first spring elements circumferentially arranged between adjacent pairs of said sinusoidally shaped web patterns to form first spring web patterns, each of said first spring elements having a first bent section located between its first and second axial ends with said first axial end of each of said first spring elements being coupled together by third web loops and said second axial end of each of said first spring elements being coupled together by fourth web loops, and said third web loops of said first spring web pattern being joined to said second web loops of said sinusoidally shaped web patterns to form a plurality of first cells of said cells of said web structure between a pair of said straight web sections and a pair of said first spring elements.

3. The expandable stent as set forth in claim 2, wherein said fourth web loops of said first spring web patterns are joined to said first web loops of said sinusoidally shaped web patterns.

4. The expandable stent as set forth in claim 2, wherein said sinusoidally shaped web patterns are all in phase with each other.

5. The expandable stent as set forth in claim 2, wherein said first bent sections of said first spring elements include a first arc with a first concavity.

6. The expandable stent as set forth in claim 2, further comprising a plurality of second spring elements circumferentially arranged between adjacent pairs of said sinusoidally shaped web patterns to form second spring web patterns, each of said second spring elements having a second bent section located between its first and second axial ends, with said first axial ends of said second spring elements being coupled together by said fourth web loops and said second axial ends of said second spring elements being coupled together by said first web loops of said sinusoidally shaped web patterns.

7. The expandable stent as set forth in claim 2, wherein said first bent sections are V-shaped.

8. The expandable stent as set forth in claim 6, wherein said first bent sections are U-shaped.

9. The expandable stent as set forth in claim 2, wherein said sinusoidally shaped web patterns are aligned in phase with one another.

10. The expandable stent as set forth in claim 2, wherein adjacent ones of said sinusoidally shaped web patterns are aligned out of phase with one another.

11. The expandable stent as set forth in claim 6, wherein adjacent ones of said sinusoidally shaped web patterns are aligned out of phase with one another.

* * * * *